United States Patent [19]
Clawson et al.

[11] Patent Number: 6,033,071
[45] Date of Patent: Mar. 7, 2000

[54] METHOD AND APPARATUS FOR MEASURING DISTANCE BETWEEN AN EYE AND A LENS

[76] Inventors: Burrell E. Clawson, 883 W. 16th St.; Richard A. Weiss, 421 San Bernardino, both of Newport Beach, Calif. 92663

[21] Appl. No.: 09/151,537

[22] Filed: Sep. 11, 1998

[51] Int. Cl.⁷ .................................................. A61B 3/10
[52] U.S. Cl. ............................................. 351/204; 33/200
[58] Field of Search ............................ 351/41, 158, 204, 351/200; 33/200

[56] References Cited

U.S. PATENT DOCUMENTS

| | | |
|---|---|---|
| 563,089 | 6/1896 | Strange . |
| 724,963 | 4/1903 | Spaulding . |
| 758,283 | 4/1904 | Shafer . |
| 1,238,045 | 8/1917 | Nelson . |
| 1,488,984 | 4/1924 | Heyne . |
| 2,694,262 | 11/1954 | Daniel . |
| 3,995,373 | 12/1976 | Brumbelow . |
| 4,177,571 | 12/1979 | Renier . |
| 5,825,459 | 10/1998 | Rubin ...................................... 351/204 |

*Primary Examiner*—Hung Xuan Dang
*Attorney, Agent, or Firm*—Stout, Uxa, Buyan & Mullins; Frank J. Uxa

[57] ABSTRACT

Methods for measuring the distance between an eye and a lens spaced apart from the eye include passing an elongated tubular structure between the eye and the lens, and causing a length of a wire member to pass out of the opening at a distal end of the elongated tubular structure. The length of the wire member extending out of the opening is selected so that the combination of the elongated tubular structure and the wire member extending out of the opening is located in close proximity to the eye and contacts the lens. This length of wire member extending out of the distal end is correlatable to the distance between the eye and the lens. Apparatus for providing such measurements are included.

22 Claims, 2 Drawing Sheets

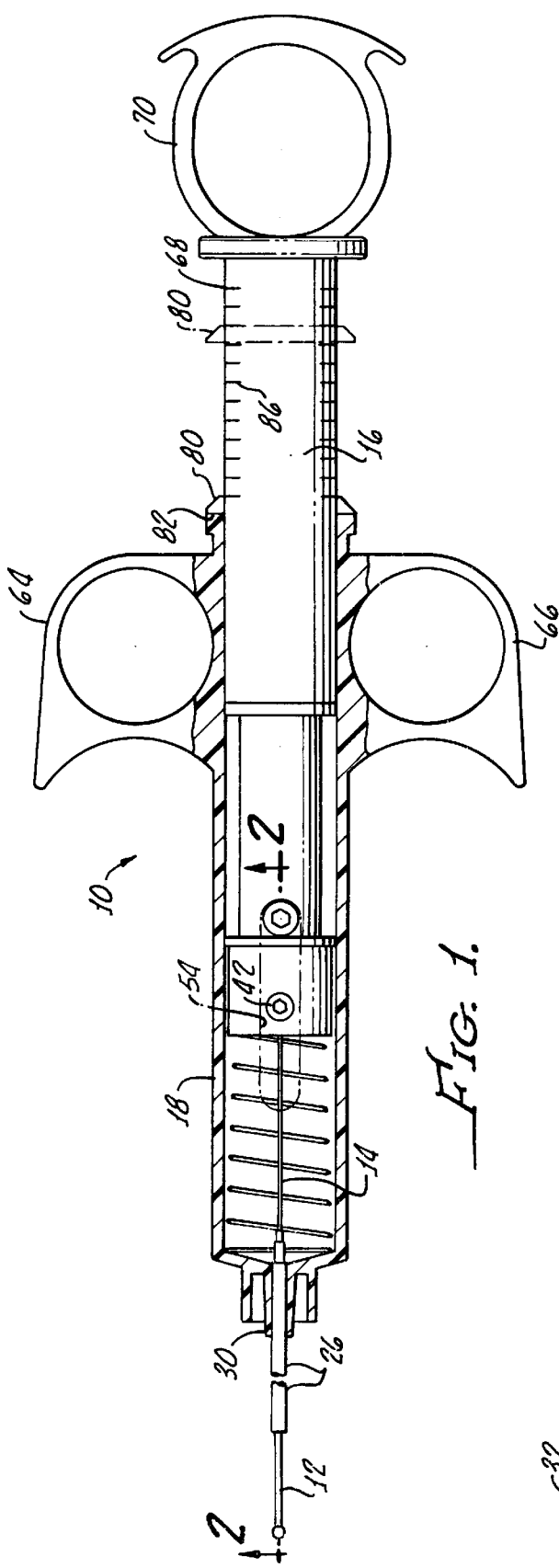
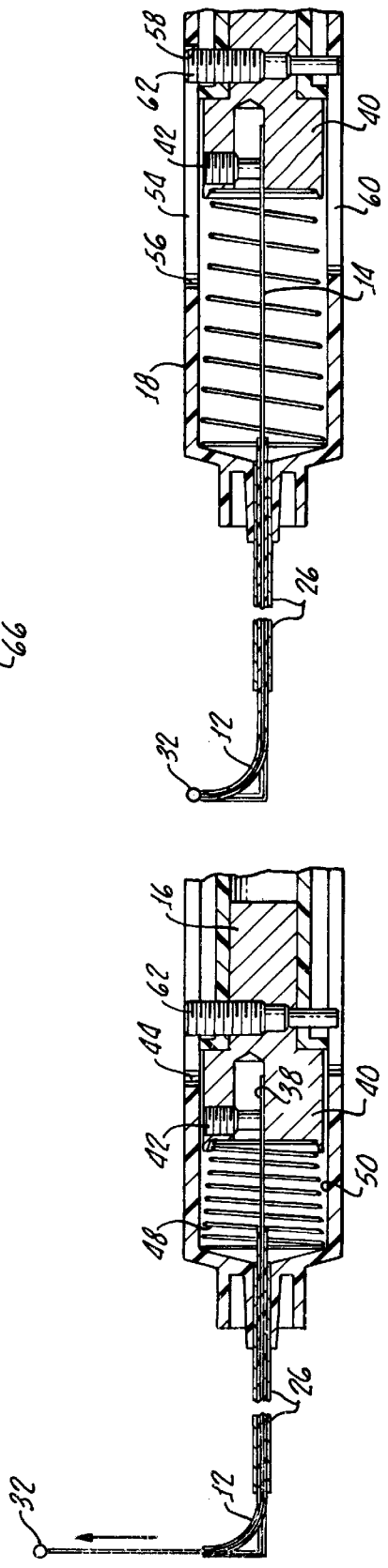
Fig. 1.
Fig. 2.
Fig. 3.

METHOD AND APPARATUS FOR MEASURING DISTANCE BETWEEN AN EYE AND A LENS

BACKGROUND OF THE INVENTION

The present invention relates to methods and apparatus for measuring distances between eyes and lenses. More particularly, the invention relates to such methods/apparatus for measuring the distance between an eye and a lens, for example, held in a phoropter or similar testing device such as a spectacle or trial frame, to facilitate the accurate prescription of a corrective lens for the eye being tested.

Many individuals require corrective lenses, e.g., eye glasses, contact lenses and the like. In order to determine the extent of the correction required, the individual's vision is tested using a phoropter or other optical measuring or testing device. In general, the testing device is placed in contact with the individual's face, for example, straddling the bridge of the nose, and the optometrist causes the individual to look through a series of lenses. This continues until the test lens providing the best vision quality is selected. The lens which is prescribed by the optometrist takes into account the optical power of the selected lens. Currently many clinicians use an average distance between the eye of the individual and the test lens (held in the testing device) is factored into the final lens prescription.

However, the actual distance between the test lens and the eye being tested varies substantially from individual to individual. This is so, for example, because of differences in facial bone structure from individual to individual. Thus, the average lens/eye distance which is customarily used in prescribing corrective lenses is only an approximation and very often introduces a diopter power error into the lens prescription.

Certain phoropters are provided with a mirror including graduations to give the clinician a measurement between the lens a nd eye. However, such graduated mirror has a limited range and is of limited usefulness, particularly in view of the restricted visibility that typically exists between the phoropter and the eye.

It would be advantageous to provide a system, for example, method and/or apparatus, for effectively measuring the distance between an individuals eye and the test lens selected as giving the best vision.

SUMMARY OF THE INVENTION

New methods and apparatus for measuring distances between eyes and lenses have been discovered. Such methods and apparatus are straightforward to practice and to construct and use. Very reliable individual eye/lens distances are provided. The distance measured is between the lens, for example, the posterior face of the lens, and the outer surface of a closed eyelid covering the eye. Importantly, such methods and apparatus are adapted to measure the eye/lens distance at the time the eye is being tested and a corrective lens is being prescribed. Thus, the distance measured is the actual eye/lens distance used in prescribing the lens. Ultimately, more accurate lens prescriptions are provided and lens wearers see more clearly and are more satisfied.

In one broad aspect of the present invention, methods for measuring the distance between an eye and a lens spaced apart from the eye are provided. Such methods comprise passing an elongated tubular structure between the eye and the lens. The elongated tubular structure has a distal end and an opening at the distal end. The methods further include causing a length of a wire member to pass out of the opening at the distal end of the elongated tubular structure. The length of the wire member extending out of the opening at the distal end is selected so that the combination of the elongated tubular structure, in particular, that portion of the tubular structure located between the eye and lens, and the wire member extending out of the opening at the distal end is located in close proximity to the eye and contacts the lens. This length of the wire member extending out of the distal end of the elongated tubular structure is correlatable to the distance between the eye and the lens. For example, by measuring the length of the wire member extending out of the distal end of the elongated tubular structure, one can easily determine the actual distance between the eye, for example, the corneal frontal or anterior surface of the eye, and the lens. For example, this actual distance can equal the length of that portion of the tubular structure located between the eye and the lens plus the length of the wire member extending out of the distal end of the tubular structure. This actual distance can then be used, for example, by an optometrist or other trained individual, to provide a corrective lens prescription to the individual whose eye has been tested.

The elongated tubular structure preferably includes a curved region proximally of the distal end of the structure. This curved region is preferably configured so that the wire member extending out of the distal end of the elongated tubular structure is oriented substantially perpendicular to the portion of the wire member located in the tubular structure proximally of the curved region. This orientation or configuration facilitates measuring the actual shortest straight line distance between the eye and the lens.

The present methods are particularly effective where the lens is being held in a phoropter or other lens testing device. More preferably, the methods are employed with the individual whose eye is being tested positioned relative to the phoropter or other testing device substantially in the same position as existed when the lens was selected as providing the best overall vision. The most accurate and/or reliable eye/lens distance is thus obtained. In order to facilitate measuring the eye/lens distance with the individual positioned in close proximity to the testing device, the elongated tubular structure preferably has a substantially constant cross-section and a length of at least about 3 inches or about 4 inches or about 5 inches or more. The relatively long tubular structure is very effective in being placed in the confined space between the eye and the phoropter or other testing device.

In another broad aspect of the present invention, apparatus for measuring the distance between an eye and a lens spaced apart from the eye are provided. In general, the apparatus comprises an elongated tubular structure, a wire member and a plunger assembly. The elongated tubular structure preferably has a distal end portion, a distal end and an opening at the distal end. The elongated tubular structure is preferably sized and adapted so that the distal end portion can be placed between the lens and the eye. The wire member has a length and is preferably sized and adapted so that at least a portion of the wire member is passable through the opening at the distal end of the tubular structure. The plunger assembly is preferably coupled to the wire member and is adapted to be moveable to pass a portion of the wire member out of the opening at the distal end.

It should be understood that the methods described herein can employ the apparatus described herein and vice versa.

The elongated tubular structure of the present apparatus preferably includes a curved portion located proximally of the distal end. The elongated tubular structure preferably has a substantially constant cross-section and a length of at least about 3 inches or about 4 inches or about 5 inches or more. The elongated tubular structure is substantially rigid in construction and may be made of any suitable material, for example, metals, polymeric materials and the like. In one very useful embodiment, the elongated tubular structure is made of metal, for example, medical grade stainless steel or other suitable metal.

The elongated tubular structure preferably includes an inner liner element made of polymeric material. Such polymeric material liner element facilitates the movement of the wire member relative to the tubular structure. In effect, the polymeric material is believed to provide some degree of natural lubricity to reduce the wear, tear and stress on the wire member as it is moved through the elongated tubular structure.

The elongated tubular structure preferably includes a curved portion located proximally of the distal end. This curved portion of the elongated tubular structure preferably is oriented so that the distal end region of the elongated tubular structure is substantially perpendicular to the proximal end region of the elongated structure. It is advantageous that the wire member extending out of the distal opening of the elongated tubular structure is substantially perpendicular to the wire member located in the tubular structure proximally of the curved portion. The distal end region of the elongated tubular structure may be oriented a few degrees short of or past perpendicular to the proximal end region of the elongated tubular structure in order to achieve the substantially perpendicular orientation of the wire member extending out of the distal opening, as described previously.

The wire member may be constructed of any suitable material or combination of materials. Because the wire member is moveable within the elongated tubular structure on a routine basis and because, in many applications, the wire member has a relatively small cross-section along its length, the wire member is subject to substantial wear, tear and stress. For example, the wire member can have a cross-sectional area, preferably a substantially constant cross-sectional area, along its length in a range of about 0.0002 square inches to about 0.0004 square inches or about 0.0025 square inches. The wire member can have any suitably configured cross-section, such as circular, rectangular and the like. In addition, the wire member preferably has a significant degree of flexibility or bendability. Therefore, some care should be given in choosing the proper material or materials of construction. In one very useful embodiment, the wire member comprises nitinol or similar materials, e.g., metals, flexible metallic-containing composite materials and the like, particularly those which can be bent repeatedly to high levels of strain without permanently deforming. This is so because the wire member preferably is repeatedly passed through the curved portion of the elongated tubular structure.

The wire member can be of any suitable length and preferably has a length in the range of about 3 inches or less to about 7 inches or about 9 inches or more. The wire member preferably is adapted to be easily replaced, for example, after breaking or being damaged, e.g., becoming kinked, so that the apparatus can continue to be used. A number of very suitable arrangements can be provided for coupling the wire member to the plunger assembly. These arrangements include, but are not limited to, the use of a chuck-type coupler, the use of a set screw and the like coupling assemblies. The coupling of the wire member to the plunger assembly preferably is such that these two components can be decoupled and a new wire member provided with no other disassembly being required. This "quick coupling/decoupling" feature facilitates rapid assembly and repair of the present apparatus.

In one very useful embodiment, the wire element includes an enlarged portion sized so as to be prevented from passing through the distal opening of the elongated tubular structure. This enlarged portion, which preferably is located at the distal end of the wire member, effectively acts as a zero point in measuring the distance between the eye and the lens. For example, the measurement is begun with the enlarged portion in direct contact with the distal opening of the elongated tubular structure. This provides a very convenient reference point from which to measure the distance or the length of the wire member which is caused to pass out of the distal opening. Also, the enlarged portion of the wire member may make distinctive or easily sensed contact with the lens, for example, contact which is easily felt by the user of the apparatus and/or is heard by the user of the apparatus. Thus, the enlarged portion of the wire member facilitates very effective and accurate distance measuring results.

The plunger assembly of the present apparatus preferably is manually operated to pass the wire member in and out of the distal opening of the elongated tubular structure. The present apparatus preferably further comprises a hollow tube in which the plunger assembly is axially moveable. In one embodiment, the hollow tube has a distal end portion to which the elongated tubular structure is secured. The plunger assembly has a proximal end section which preferably extends proximally of the hollow tube. The combination of the plunger assembly and the hollow tube preferably is manually operated to effect the in and out movement of the wire member, as described herein. In one embodiment, the hollow tube includes at least one finger grip member, preferably two finger grip members. The plunger assembly may include at least one thumb grip. Thus, in one very useful embodiment, the user of the apparatus grips the hollow tube using two fingers and grips the plunger assembly using the thumb grip. This allows the user to very conveniently place the apparatus between the eye and the lens and to control the release of the wire member so that the distance between the eye and the lens can be effectively and accurately measured.

In one useful embodiment, the plunger assembly or the hollow tube includes a distance scale, that is a measuring scale for identifying distance, adapted to facilitate indicating the distance the plunger assembly has been moved distally in the hollow tube. A measuring assembly preferably is included and is located on at least one of the hollow tube and the plunger assembly and is adapted to provide an indication of the distance the plunger assembly is moved into the hollow tube. This measuring assembly preferably includes an indicator member adapted to be placed in contact with the hollow tube when the plunger member is being moved distally into the hollow tube and to be carried by or ride the plunger assembly when the plunger assembly is moved proximally relative to the hollow tube. In one very useful embodiment, the indicator member is a moveable ring structure located around the plunger assembly. More preferably, the plunger assembly includes a distance scale, which is adapted, together with an indicator member located on the plunger assembly, to indicate the distance the plunger assembly has been moved distally into the hollow tube.

The hollow tube may include an axially extending, through slot. This through slot preferably is closed at both longitudinally spaced apart ends. In this embodiment, the plunger assembly preferably includes a projection extending into the through slot. The projection and the through slot cooperate to limit the axial movement of the plunger assembly relative to the hollow tube. This feature effectively maintains the apparatus in an assembled condition and, at the same time, reduces the stress on the wire member caused by excessive pulling of the plunger assembly relative to the hollow tube.

In the event that a set screw arrangement is used to couple the wire member to the plunger assembly, the through slot noted above can be sized and positioned so that the set screw is accessible from the through slot. This very conveniently allows the wire member to be replaced with minimal additional disassembly of the present apparatus. This feature is very useful in maintaining the apparatus operating with a minimum of disruption even when the wire member has been broken or otherwise rendered ineffective.

A bias member, for example, a spring member, may be located in the hollow tube, preferably in the distal portion of the hollow tube, and is adapted to urge the plunger assembly proximally in the hollow tube. This feature reduces the risk of injuring the person whose eyes are being tested by overextending the wire member or otherwise pushing the elongated tubular structure toward the eye being tested. Also, the bias member facilitates maintaining the indicator member, e.g., ring structure, in its correct position during removal of the apparatus from between the eye and the lens and prior to reading the measuring scale.

In a useful embodiment, an angled support member preferably is included. This angled support member is secured to the elongated tubular structure at or near the curved region. This support member preferably is positioned so that the tubular member can be placed in contact with the eyelid of the eye being tested with little or no risk of harming the eye. In addition, the support member preferably increases the accuracy of the lens/eye distance measurement.

Any feature or combination of features described herein is included within the scope of the present invention provided that the features of any such combination are not mutually inconsistent.

Additional aspects and advantages of the present invention are set forth in the following description and claims, particularly when considered in conjunction with the accompanying drawing in which like parts bear like reference numerals.

BRIEF DESCRIPTION OF THE DRAWINGS

FIG. 1 is a top plan view, partially in cross-section, of an embodiment of an apparatus in accordance with the present invention.

FIG. 2 is a cross-sectional view taken generally along line 2—2 of FIG. 1.

FIG. 3 is a partial cross-sectional view of the embodiment shown in FIG. 1 with an increased amount of wire member extended.

DETAILED DESCRIPTION OF THE DRAWINGS

Figure 4:
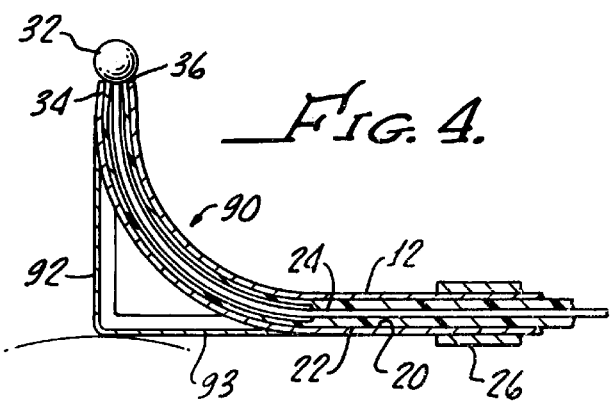
FIG. 4 is a detailed cross-sectional view of the distal end region of the elongated tubular structure and associated components.

With reference to FIGS. 1 to 4, an eye/lens distance measuring apparatus in accordance with the present invention, shown generally at 10, includes an elongated tube 12, a wire member 14, a plunger 16 and a hollow housing tube 18.

Elongated tube 12 defines an open ended hollow space 20 in which is located a hollow inner liner 22 and the distal portion 24 of wire member 14. A protective collar 26 surrounds the central portion of elongated tube 12. Although any suitable materials of construction may be used, as shown elongated tube 12 and collar 26 are made of stainless steel, wire member 14 is made of a metal such as nitinol and the inner liner 22 is made of a polyflourohydrocarbon, such as Teflon®.

Protective collar 26 is adhered or otherwise secured to elongated tube 12. Inner liner 22 is adhered or otherwise secured to the inner sidewall of the elongated tube. Inner liner 22 facilitates the passage of wire member 14 through the elongated tube 12.

The protective collar 26 is coupled to the distal end 30 of hollow housing tube 18. This coupling can be by the use of adhesives or a friction or interference fit. In any event, protective collar 26 and elongated tube 12 are firmly secured to housing tube 18.

The distal end of wire member 14 includes an enlarged element or ball 32 which is of sufficient size so as to be incapable of passing through the distal opening 34 at the distal end 36 of the elongated tube 12. The enlarged element 32 provides an effective zero point for the apparatus 10 in that the element 32 is the only part of wire member 14 extending out of the distal opening 34 when the element 32 is in contact with distal end 36.

The proximal end portion 38 of wire member 14 is coupled to the distal end segment 40 of plunger assembly 16 using set screw 42. To couple the proximal end region 38 of wire member 14 to distal end segment 40, the set screw 42 is screwed into a threaded bore 44 in distal end segment 40. This threading continues until set screw 42 comes in contact with proximal end region 38 of wire member 14 to hold the proximal end region secured to distal end segment 40 of plunger assembly 16.

A spring member 48 is located in hollow space 50 defined by hollow housing tube 18. Spring member 48, which is located distally of plunger assembly 16, acts to bias the plunger assembly proximally, as shown in FIGS. 1 and 2.

Hollow housing tube 18 includes a through slot 54 which is closed at both ends 56 and 58. A similarly sized second through slot 60 is located directly opposite through slot 54 in housing tube 18. A threaded pin 62 is secured to plunger assembly 16 and is sized to extend into both slots 54 and 60. The combination of pin 62 and slots 54 and 60 act to limit the axial movement of plunger assembly 16 relative to housing tube 18. For example, in the fully retracted position of wire member 14, as shown in FIG. 2, the pin 62 is in contact with the proximal end 58 of slot 54. Thus, plunger assembly 16 can move no further proximally relative to hollow housing tube 18. This reduces the stress on wire element 14 and reduces the risk of breakage of wire element 14. Similarly, in the fully extended position of wire element 14 (not shown) the pin 62 is in contact with distal end 56 of slot 54 so as to prevent further distal movement of plunger assembly 16 relative to hollow housing tube 18.

One additional feature of the present invention, illustrated in FIG. 2, involves assembling the wire member 14 or replacing the wire member 14 with the remaining components of the apparatus 10 already in place. Thus, as shown in FIG. 2, with the wire element 14 in its fully retracted position, set screw 42 is readily accessible through slot 54.

Thus, set screw 42 can be either loosened or tightened to decouple or couple wire member 14 (or a replacement wire member) to the distal segment 40 of plunger assembly 16. This quick assembly feature very effectively allows wire member 14 to be replaced so as to reduce downtime caused by the breakage of wire member 14.

Hollow housing tube 18 includes two oppositely disposed finger gripping members 54 and 56. The proximal end portion 68 of plunger assembly 16 includes a thumb gripping member 70. The combination of finger gripping members 54 and 56 and thumb gripping member 70 allows the user of apparatus 10 to conveniently manipulate, for example, rotate, the apparatus 10 as necessary to properly place the tubular member 12 between the eye and the lens and to provide for controlled movement of the plunger assembly 16 relative to the hollow housing tube 18, as desired.

A measuring ring 80 is located around plunger assembly 16 proximally of hollow housing tube 18. As shown in FIG. 1, measuring ring 80 is positioned in contact with the proximal end 82 of hollow housing tube 18. This is the position measuring ring 80 occupies when wire element 14 is in the fully retracted position, as shown in FIG. 2.

As plunger assembly 16 is passed into hollow housing tube 18, measuring ring 80 is maintained stationary in place in contact with proximal end 82 of housing tube 18. Thereafter, plunger assembly 16 is moved proximally relative to housing tube 18. This movement causes measuring element 80 to be carried by or ride on plunger assembly 16 so that once plunger assembly is back to its proximal-most position, measuring ring 80 is positioned as shown in the shadow lines in FIG. 1. Plunger assembly 16 includes a distance measuring scale 86. Measuring ring 80, in combination with distance scale 86, allows the user of apparatus 10 to determine the distance that plunger assembly 16 has been moved distally relative to housing tube 18. As is discussed hereinafter, this distance is correlatable to the distance between an eye and a lens which is spaced apart from the eye.

Elongated tube 12 includes a curved region 90 which bends the elongated tube 12 through an angle of about 90°. The curved region 90 is designed so that the wire member 14 extending out of the distal opening 34 of elongated tube 12 is oriented substantially perpendicular to the proximal end portion 38 of the wire member 14. In addition, a right angled support element 92 is secured to the elongated tube 12 about the outside of the curved portion 90, as shown best in FIG. 4. This right angled support element 92 provides for enhanced eye/lens distance measurement, as is discussed hereinafter. The straightline distance between the laterally extending leg 93 of support element 92 and distal end 36 of elongated tube 12 preferably is in the range of about 5 mm to about 15 mm. The maximum length of wire member 14 extending out of distal opening 34 preferably is in the range of about 5 mm to about 40 mm.

Figure 5:
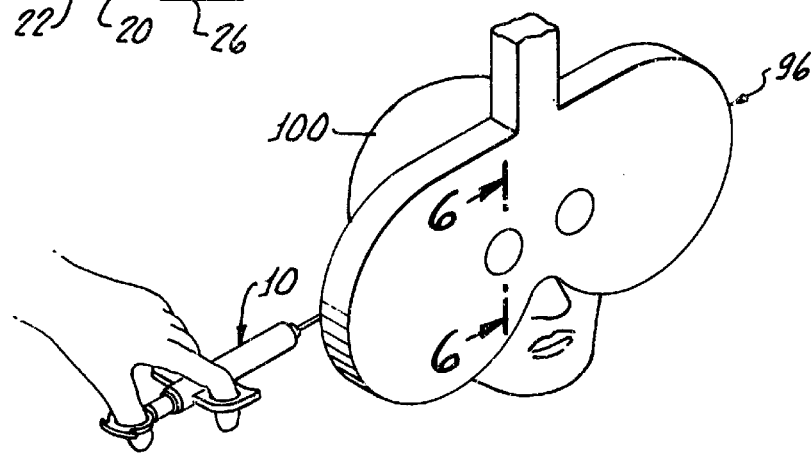
FIG. 5 is a perspective view of the embodiment shown in FIG. 1 in use.
Figure 6:
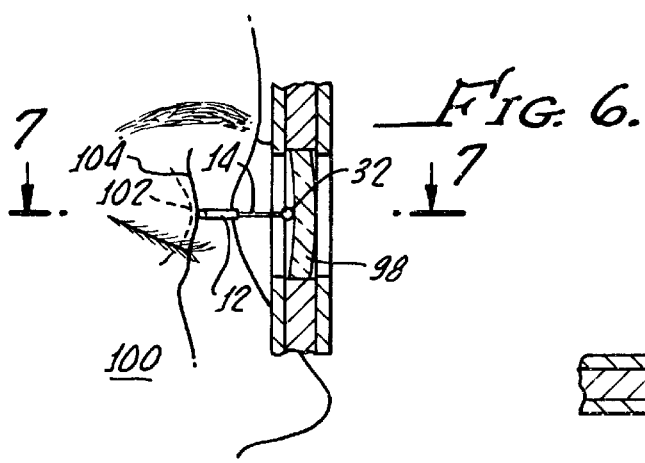
FIG. 6 is a view, partially in cross-section, taken generally along line 6—6 of FIG. 5.
Figure 7:
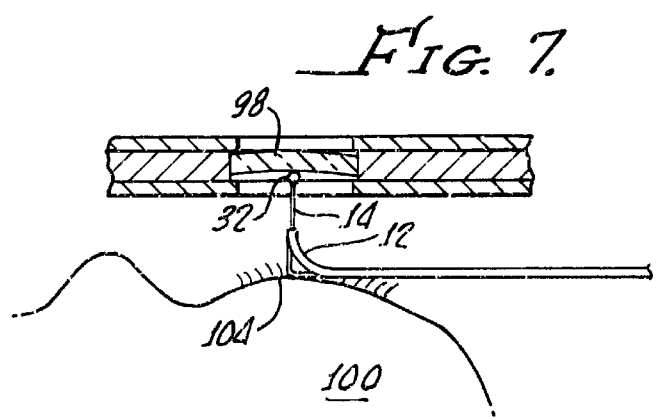
FIG. 7 is a view, partially in cross-section, taken generally along line 7—7 of FIG. 6.

FIGS. 5, 6 and 7 illustrate the use of apparatus 10. Specifically, FIGS. 5–7 show an individual 100 being fitted with corrective lenses using phoropter 96. Once a selected lens 98 has been identified as providing the best vision quality for the individual 100, apparatus 10 is used to determine the actual distance between the lens 98 and the eye 102 of the individual 100.

With the phoropter 96 and individual 100 remaining in the same place as when the lens 98 was selected, the user of apparatus 10 places the distal end portion of the apparatus between the phoropter 96 and the closed eyelid 104 of the individual 100. The angled support element 92 is placed in contact with the eyelid 104 of the individual 100, as shown best in FIG. 7. The plunger assembly 16 is moved distally relative to housing tube 18 until the wire member 14 extends from the elongated tube 12 and to the point where element 32 contacts lens 98. Once that contact has been made with angled element 92 touching eyelid 104, the plunger assembly 16 is retracted or moved proximally relative to housing tube 18 and the apparatus 10 is removed from between the phoropter 96 and individual 100.

By noting the position of measuring ring 80 relative to distance scale 86, the user of apparatus 10 can determine how far plunger assembly 16 has been moved distally relative to housing tube 18. This distance is correlatable with the distance between the eye 102 of individual 100 and lens 98 being held by phoropter 96. For example, if the distance on the distance scale is identified as zero with the measuring ring 80 in contact with the housing tube 18, then the distance identified after use of the instrument will need to be increased by the length of the distal end portion of the apparatus which had been positioned between the phoropter 96 and the closed eyelid 104 and by approximately 3 mm to take into account the thickness of eyelid 104. On the other hand, the scale 86 can be adjusted to automatically take into account this length of the distal end portion of the apparatus which had been positioned between the phoropter 96 and the closed eyelid 104 and/or the thickness of eyelid 104.

In any event, the distance between the eye 102 of individual 100 and the lens 98 can be easily determined using apparatus 10. This distance, which is specific to individual 100, rather than being an average distance as conventionally employed, is taken into account when providing the prescription for a corrective lens for individual 100. Ultimately, the prescription is more accurate (then the prescription using an average eye/lens distance) and the individual sees more clearly and is more satisfied.

While this invention has been described with respect to various specific examples and embodiments, it is to be understood that the invention is not limited thereto and that it can be variously practiced within the scope of the following claims.

What is claimed is:

1. A method for measuring the distance between an eye and a lens spaced apart from the eye, the method comprising:

passing an elongated tubular structure between the eye and the lens, the elongated tubular structure having a distal end and an opening at the distal end; and causing a length of a wire member to pass out of the opening at the distal end, the length of the wire member extending out of the opening at the distal end being selected so that the combination of the elongated tubular structure and the wire member is located in close proximity to the eye and contacts the lens, the length of the wire member extending out of the distal end being correlatable to the distance between the eye and the lens.

2. The method of claim 1 which further comprises determining the length of the wire member extending out of the distal end.

3. The method of claim 1 wherein the length of the wire member extending out of the opening at the distal end is selected so that the elongated tubular member is in contact with a closed eyelid covering the eye and the wire member contacts the lens.

4. The method of claim 1 wherein the elongated tubular structure includes a curved region proximally of the distal end and the lens is located directly in front of the eye.

5. The method of claim 1 wherein the elongated tubular structure has a length of at least about 5 inches.

6. The method of claim 1 wherein the lens is held in an optical measuring device.

7. An apparatus for measuring the distance between an eye and a lens spaced apart from the eye, the apparatus comprising:

an elongated tubular structure having a distal end portion, a distal end and an opening at the distal end, and being sized and adapted so that the distal end portion can be placed between the lens and the eye;

a wire member having a length and being sized and adapted so that at least a portion of the wire member is passable through the opening at the distal end; and a plunger assembly coupled to the wire member and being adapted to be movable to pass a portion of the wire member in or out of the opening at the distal end.

8. The apparatus of claim 7 wherein the elongated tubular structure has a length of at least about 5 inches.

9. The apparatus of claim 7 wherein the elongated tubular structure includes an inner liner element comprising polymeric material, and the wire member comprises metal.

10. The apparatus of claim 7 wherein the wire member includes an enlarged portion sized so as to be prevented from passing through the distal opening of the elongated tubular structure.

11. The apparatus of claim 7 which further comprises a set screw positioned and adapted to cooperate with the plunger assembly to couple the wire member to the plunger assembly.

12. The apparatus of claim 7 wherein the elongated tubular structure includes a curved region proximally of the distal end and oriented so that the distal end region of the elongated tubular structure is substantially perpendicular to the proximal end region of the elongated tubular structure.

13. The apparatus of claim 12 which further comprises an angled support member secured to the elongated tubular structure at or near the curved region.

14. The apparatus of claim 7 which further comprises a hollow tube in which the plunger assembly is axially movable, the hollow tube having a distal end portion to which the elongated tubular structure is secured.

15. The apparatus of claim 14 wherein the hollow tube includes at least one finger grip member, and the plunger assembly includes at least one thumb grip member.

16. The apparatus of claim 14 which further comprises a measuring assembly located on at least one of the hollow tube and the plunger assembly and adapted to provide an indication of the distance the plunger assembly is moved into the hollow tube.

17. The apparatus of claim 16 wherein the measuring assembly includes an indicator member adapted to be placed in contact with the hollow tube when the plunger assembly is being moved distally into the hollow tube and to be carried on the plunger assembly when the plunger assembly is moved proximally relative to the hollow tube.

18. The apparatus of claim 17 wherein the plunger assembly includes a distance scale which is adapted, together with the indicator member, to indicate the distance the plunger assembly has been moved distally in the hollow tube.

19. The apparatus of claim 14 wherein the hollow tube includes an axially extending through slot, and the plunger assembly includes a projection extending into the through slot, the projection and the through slot cooperating to limit the axial movement of the plunger assembly relative to the hollow tube.

20. The apparatus of claim 19 which further comprises a set screw positioned and adapted to cooperate with the plunger assembly to couple the wire member to the plunger assembly, provided that the through slot is sized and positioned so that the set screw is accessible from the through slot.

21. The apparatus of claim 14 which further comprises a bias member located in the hollow tube and adapted to urge the plunger assembly proximally in the hollow tube.

22. The apparatus of claim 14 wherein the plunger assembly or the hollow tube includes a distance scale adapted to facilitate indicating the distance the plunger assembly has been moved distally in the hollow tube.

* * * * *